(12) United States Patent
Ogasawara et al.

(10) Patent No.: US 11,076,793 B2
(45) Date of Patent: Aug. 3, 2021

(54) RESPIRATION ESTIMATION METHOD AND APPARATUS

(71) Applicant: NIPPON TELEGRAPH AND TELEPHONE CORPORATION, Tokyo (JP)

(72) Inventors: Takayuki Ogasawara, Kanagawa (JP); Takuro Tajima, Kanagawa (JP); Kei Kuwabara, Kanagawa (JP); Nobuaki Matsuura, Kanagawa (JP); Ryoichi Kasahara, Kanagawa (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 300 days.

(21) Appl. No.: 15/774,964

(22) PCT Filed: Nov. 4, 2016

(86) PCT No.: PCT/JP2016/082799
§ 371 (c)(1),
(2) Date: May 9, 2018

(87) PCT Pub. No.: WO2017/082165
PCT Pub. Date: May 18, 2017

(65) Prior Publication Data
US 2018/0333064 A1 Nov. 22, 2018

(30) Foreign Application Priority Data
Nov. 10, 2015 (JP) .............................. JP2015-220157

(51) Int. Cl.
*A61B 5/08* (2006.01)
*A61B 5/316* (2021.01)
(Continued)

(52) U.S. Cl.
CPC ............ *A61B 5/316* (2021.01); *A61B 5/0816* (2013.01); *A61B 5/113* (2013.01); *A61B 5/352* (2021.01);
(Continued)

(58) Field of Classification Search
None
See application file for complete search history.

(56) References Cited

U.S. PATENT DOCUMENTS 5,105,354 A * 4/1992 Nishimura ........... A61B 5/0205
600/484
8,430,817 B1 * 4/2013 Al-Ali .................... A61B 5/746
600/301
(Continued)

FOREIGN PATENT DOCUMENTS

CN 101815465 A 8/2010
JP 2010-540124 A 12/2010
(Continued)

OTHER PUBLICATIONS

Supplementary European Search Report and Written Opinion Received for EP Application No. 16864128.0, dated Jun. 11, 2019, 10 pages.
(Continued)

*Primary Examiner* — Etsub D Berhanu
*Assistant Examiner* — Aurelie H Tu
(74) *Attorney, Agent, or Firm* — Womble Bond Dickinson (US) LLP

(57) ABSTRACT

There is provided a respiration estimation apparatus. The respiration estimation apparatus includes an R-wave amplitude detection unit (5) configured to detect an amplitude of an R wave from a cardiac potential waveform of a subject, an R-R interval detection unit (6) configured to detect an R-R interval as an interval between an R wave and an immediately preceding R wave from the cardiac potential
(Continued)

waveform, an acceleration displacement detection unit (7) configured to detect an angular displacement of an acceleration vector from a triaxial acceleration signal by a respiratory motion of the subject, a Fourier transform unit (10) configured to Fourier-transform each of time-series signals of the R-wave amplitude, the R-R interval, and the angular displacement to obtain a frequency spectrum of each of the signals of the R-wave amplitude, the R-R interval, and the angular displacement, and a signal selection unit (11) configured to extract a frequency as a candidate of a respiration frequency of the subject from each of the frequency spectrum of the R-wave amplitude, the frequency spectrum of the R-R interval, and the frequency spectrum of the angular displacement, and select best data from the frequencies as the respiration frequency of the subject.

2 Claims, 8 Drawing Sheets

(51) Int. Cl.
*A61B 5/00* (2006.01)
*A61B 5/352* (2021.01)
*A61B 5/113* (2006.01)

(52) U.S. Cl.
CPC .......... *A61B 5/7221* (2013.01); *A61B 5/7257* (2013.01); *A61B 5/7278* (2013.01); *A61B 5/6804* (2013.01)

(56) References Cited

U.S. PATENT DOCUMENTS

| | | | |
|---|---|---|---|
| 2005/0131478 A1* | 6/2005 | Kim | A61B 5/7264 607/27 |
| 2006/0041201 A1* | 2/2006 | Behbehani | A61B 5/0456 600/521 |
| 2010/0004552 A1 | 1/2010 | Zhang et al. | |
| 2010/0217133 A1 | 8/2010 | Nilsen et al. | |
| 2011/0118620 A1* | 5/2011 | Scheib | A61B 5/048 600/544 |
| 2011/0160967 A1* | 6/2011 | Moench | B60T 7/22 701/45 |
| 2011/0257553 A1* | 10/2011 | Banet | A61B 5/0816 600/536 |
| 2012/0125337 A1* | 5/2012 | Asanoi | A61B 5/4812 128/204.23 |
| 2014/0228692 A1 | 8/2014 | Chan et al. | |
| 2015/0272474 A1* | 10/2015 | Genc | A61B 5/7203 600/484 |
| 2018/0344208 A1* | 12/2018 | Ogasawara | A61B 5/08 |

FOREIGN PATENT DOCUMENTS

| | | |
|---|---|---|
| JP | 2015-083045 A | 4/2015 |
| KR | 10-2010-0045521 A | 5/2010 |
| WO | WO 2009/043087 A1 | 4/2009 |
| WO | 2013/033393 A1 | 3/2013 |

OTHER PUBLICATIONS

International Search Report and Written Opinion received for PCT Patent Application No. PCT/JP2016/082799, dated Dec. 13, 2016, 11 pages (5 pages of English Translation and 6 pages of Original Document).

International Preliminary Report on Patentability received for PCT Patent Application No. PCT/JP20161082799, dated May 24, 2018, 10 pages (6 pages of English Translation and 4 pages of Original Document).

A.M. Chan, N. Ferdosi, and R. Narasimhan, "Ambulatory Respiratory Rate Detection using ECG and a Triaxial Accelerometer", 35th Annual International Conference of the IEEE EMBS, pp. 4058-4061, Jul. 2013, pp. 4058-4061.

"ECG Implementation on the TMS320C5515 DSP Medical Development Kit (MDK) with the ADS1298 ECG-FE", Texas Instruments Incorporated, <http://www.ti.com/lit/an/sprabj1/sprabj1.pdf>, 2011.

A. Bates, M.J. Ling, J. Mann and D.K. Arvind, "Respiratory rate and flow waveform estimation from tri-axial accelerometer data", International Conference on Body Sensor Network, pp. 144-150, Jun. 2010.

* cited by examiner

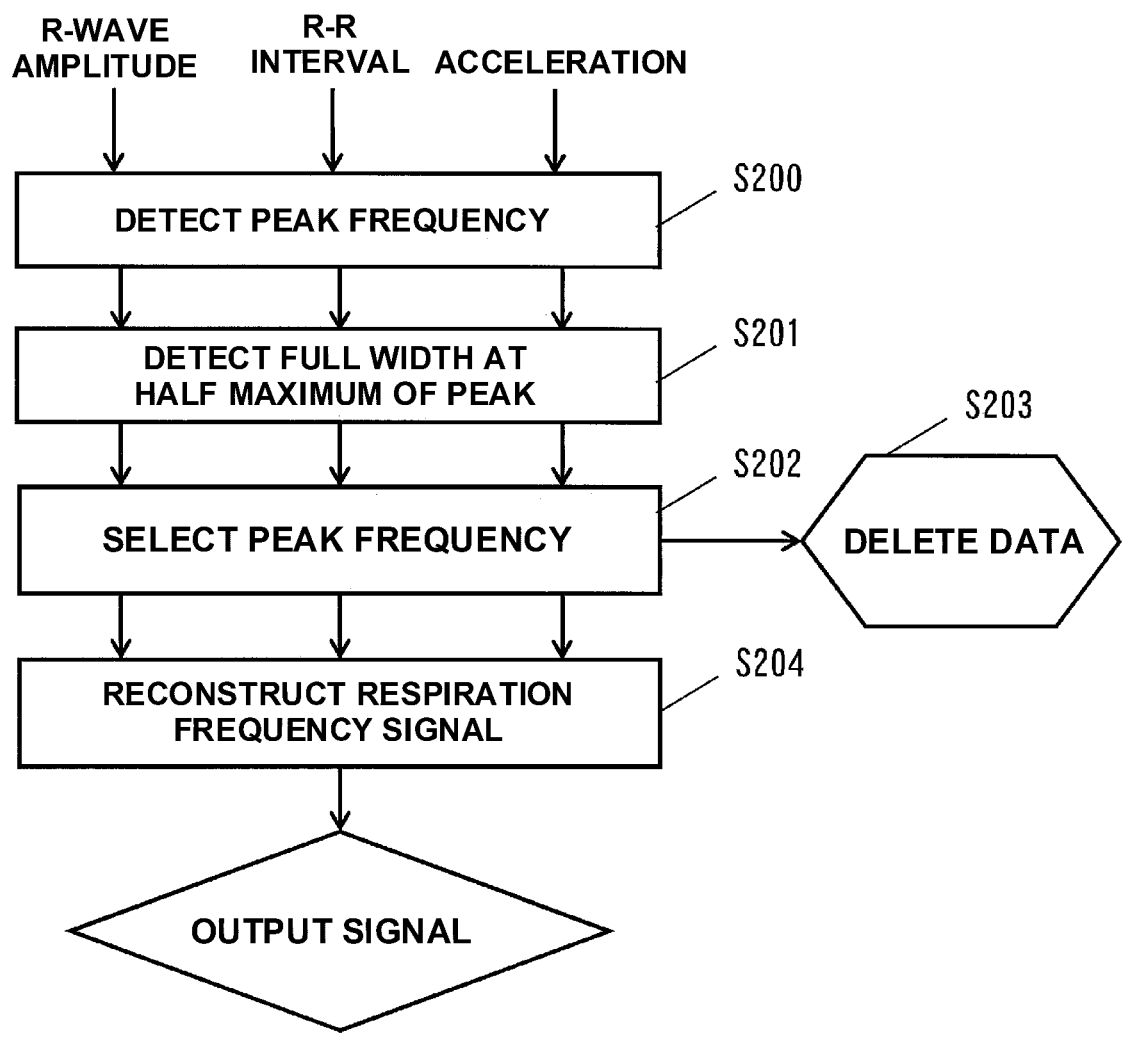

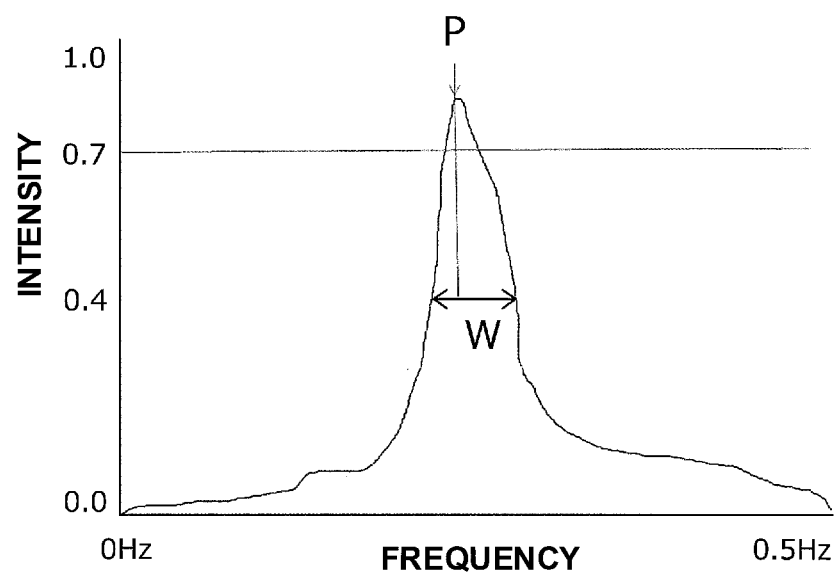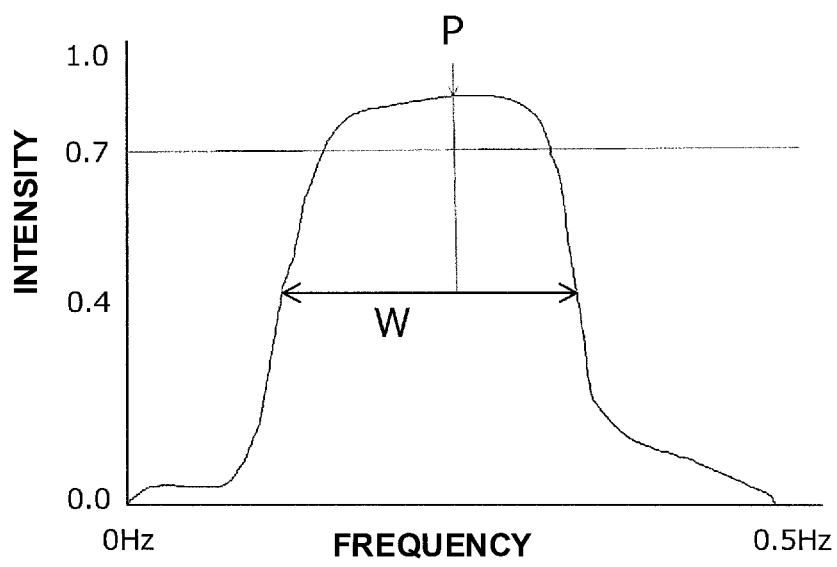

RESPIRATION ESTIMATION METHOD AND APPARATUS

TECHNICAL FIELD

The present invention relates to a respiration estimation method and apparatus for estimating the respiration condition of a subject using a biological information sensor.

BACKGROUND ART

Continuous respiratory monitoring of continuously observing breathing of a person is expected to be applied to diagnosis of respiratory diseases, the rehabilitation of a patient with a respiratory disease, remote monitoring of a fetus or patient, stress diagnosis, and the like. As a general respiration measurement method, a respiratory flow meter by a mask, heat measurement by a thermistor arranged in the nasal cavity, a chest deflection measurement band, an electrical impedance meter for a chest, or the like is used. These methods pose a problem that a subject has an unnatural feeling when wearing the device.

On the other hand, in recent years, along with the progress of wearable devices, there have been developed devices that give an improved wearing feeling to a human body. For example, there is proposed a wearable sensor in which electrodes 101 and 102 are embedded in clothing 100 such as a shirt, as shown in FIG. 8 (patent literature 1). This wearable sensor functions as a wearable electrocardiograph by arranging, near a heart 103, the electrodes 101 and 102 made of conductive fiber, and connecting the electrodes 101 and 102 to terminals (not shown) via wiring lines.

Attempts have been made to estimate the respiration condition of a person from a cardiac potential. However, when an attempt is made to estimate the respiration condition of a subject using an R-R interval as the interval between the R wave and the immediately preceding R wave of a cardiac potential, the influence of the autonomic nervous system of the subject becomes significantly apparent, and an estimation result changes depending on the age of the subject or the mental condition of the subject at the time of measurement or whether it is before or after the measurement. When an attempt is made to estimate the respiration condition of a subject using the R-wave amplitude of a cardiac potential, a measurement error occurs in accordance with a change in contact impedance between the electrode and the skin, that is caused by the body motion or skin condition of the subject, or the individual difference of the body structure or skin condition of the subject.

Thus, for example, non-patent literature 1 discloses a method of estimating the respiration condition (breathing rate) of a subject based on acceleration data of the subject in addition to conventional electrocardiograph data. The method disclosed in non-patent literature 1 improves estimation accuracy by obtaining the weighted mean of three indices of the R-R interval, R-wave amplitude, and acceleration of a cardiac potential. In the method disclosed in non-patent literature 1, when $BR_{RSA}$ represents a respiratory rate estimated from the R-R interval, $BR_{QRSa}$ represents a respiratory rate estimated from the R-wave amplitude, and $BR_{accel}$ represents a respiratory rate estimated from the acceleration data, a respiratory rate $BR_{combined}$ obtained by the weighted mean of the above respiratory rates is given by:

$$BR_{combined} = (Q_{RSA} BR_{RSA} + Q_{QRSa} Br_{QRSa} + Q_{accel} BR_{QRSa})/(Q_{RSA} + Q_{QRSa} + Q_{accel}) \quad (1)$$

The weighting constants $Q_{RSA}$, $Q_{QRSa}$, and $Q_{accel}$ of equation (1) change depending on the respective indices of the R-R interval, R-wave amplitude, and acceleration, and are adjusted within the range of 0 to 1 depending on the signal quality. By peak detection of time-series data, an error constant E is calculated as the linear sum of four parameters, that is, the standard deviation of peak amplitudes, the average value of the peak amplitudes, a time-varying constant between minimum values, and the ratio between the number of maximum and minimum values and the total number of maximum and minimum values, and signal quality Q is given by:

$$Q = \exp\{-(E/\tau)\} \quad (2)$$

where $\tau$ represents an empirically determined constant. Note that if the signal amplitude is set as a noise level, Q is set to zero.

In the method disclosed in non-patent literature 1, since a respiratory sampling interval is restricted by the cardiac cycle, it is difficult to measure a pneumogram with a short cycle. Furthermore, in the method disclosed in non-patent literature 1, variations of the R-wave amplitude of the cardiac potential and variations of the signal waveform amplitude of the accelerator also occur due to an artifact caused by the body motion of the subject, and a constant to be used to calculate the respiratory rate needs to be changed in accordance with the individual difference. Hence, the SN (Signal-to-Noise) ratio does not always improve, and respiration estimation accuracy cannot be improved.

RELATED ART LITERATURE

Patent Literature

Patent Literature 1: Japanese Patent Laid-Open No. 2015-83045

Non-Patent Literature

Non-Patent Literature 1: A. M. Chan, N. Ferdosi, and R. Narasimhan, "Ambulatory Respiratory Rate Detection using ECG and a Triaxial Accelerometer", 35th Annual International Conference of the IEEE EMBS, pp. 4058-4061, July, 2013

Disclosure of Invention

Problem to be Solved by the Invention

The present invention has been made in consideration of the above problems, and has as its object to provide a respiration estimation method and apparatus capable of improving respiration estimation accuracy under various conditions.

Means of Solution to the Problem

According to the present invention, there is provided a respiration estimation method comprising:
an R-wave amplitude detection step of detecting an amplitude of an R wave from a cardiac potential waveform of a subject, an R-R interval detection step of detecting an R-R interval as an interval between an R wave and an immediately preceding R wave from the cardiac potential waveform of the subject, an acceleration displacement detection step of detecting an angular displacement of an acceleration vector from a triaxial acceleration signal by a respiratory motion of the subject, a Fourier transform step of Fourier-transforming each of a time-series signal of the R-wave amplitude, a time-series signal of the R-R interval, and a time-series signal of the angular displacement to obtain a frequency spectrum of each of the signals of the R-wave amplitude, R-R interval, and the angular displacement, and a signal selection step of extracting a frequency as a candidate of a respiration frequency of the subject from each of the frequency spectrum of the R-wave amplitude, the frequency spectrum of the R-R interval, and the frequency spectrum of the angular displacement, all of which have been obtained in the Fourier transform step, and selecting best data from the frequencies as the respiration frequency of the subject.

According to the present invention, there is also provided a respiration estimation apparatus comprising an R-wave amplitude detection unit configured to detect an amplitude of an R wave from a cardiac potential waveform of a subject, an R-R interval detection unit configured to detect an R-R interval as an interval between an R wave and an immediately preceding R wave from the cardiac potential waveform of the subject, an acceleration displacement detection unit configured to detect an angular displacement of an acceleration vector from a triaxial acceleration signal by a respiratory motion of the subject, a Fourier transform unit configured to Fourier-transform each of a time-series signal of the R-wave amplitude, a time-series signal of the R-R interval, and a time-series signal of the angular displacement to obtain a frequency spectrum of each of the signals of the R-wave amplitude, the R-R interval, and the angular displacement, and a signal selection unit configured to extract a frequency as a candidate of a respiration frequency of the subject from each of the frequency spectrum of the R-wave amplitude, the frequency spectrum of the R-R interval, and the frequency spectrum of the angular displacement, all of which have been obtained by the Fourier transform unit, and select best data from the frequencies as the respiration frequency of the subject.

Effect of the Invention

According to the present invention, by extracting a frequency as a candidate of the respiration frequency of a subject from each of the frequency spectrum of an R-wave amplitude, that of an R-R interval, and that of an angular displacement, and selecting the best data from the frequencies as the respiration frequency of the subject, it is possible to estimate the respiration frequency of the subject with respect to the individual difference or a wide variety of measurement conditions, and reduce the influence of the artifact of the body motion of the subject, thereby improving respiration estimation accuracy.

BRIEF DESCRIPTION OF DRAWINGS

FIG. 4 is a flowchart for explaining the operation of the signal selection unit of the respiration estimation apparatus according to the embodiment of the present invention;

FIGS. 5A and 5B are graphs each showing an example of a frequency spectrum as a result of Fourier-transforming data according to the embodiment of the present invention;

BEST MODE FOR CARRYING OUT THE INVENTION

Figure 1:
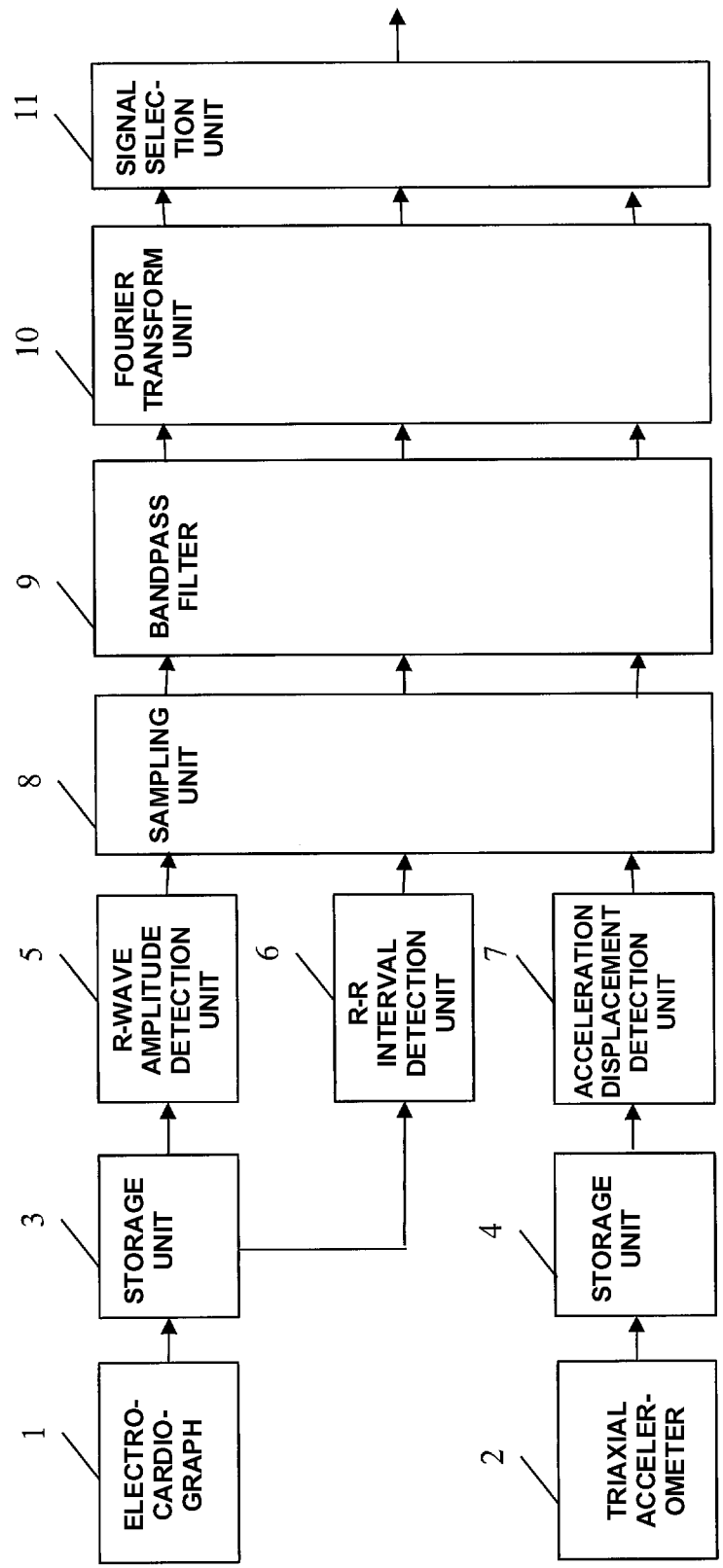
FIG. 1 is a block diagram showing the arrangement of a respiration estimation apparatus according to an embodiment of the present invention.

An embodiment of the present invention will be described below with reference to the accompanying drawings. FIG. 1 is a block diagram showing the arrangement of a respiration estimation apparatus according to the embodiment of the present invention. The respiration estimation apparatus includes an electrocardiograph 1, a triaxial accelerometer 2, storage units 3 and 4, an R-wave amplitude detection unit 5, an R-R interval detection unit 6, an acceleration displacement detection unit 7, a sampling unit 8, a bandpass filter 9, a Fourier transform unit 10, and a signal selection unit 11.

Figure 2:
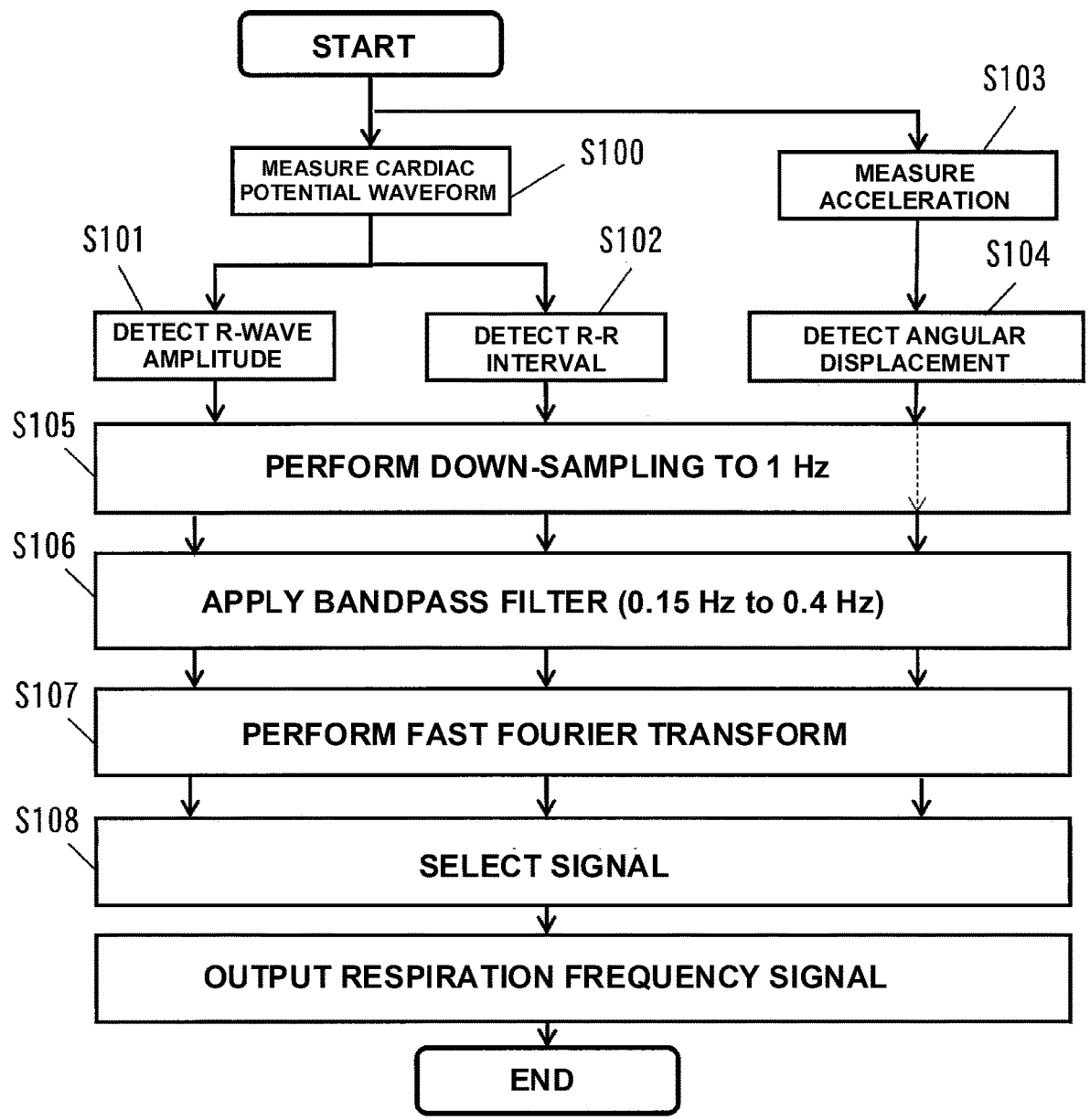
FIG. 2 is a flowchart for explaining the operation of the respiration estimation apparatus according to the embodiment of the present invention.

FIG. 2 is a flowchart for explaining the operation of the respiration estimation apparatus. The electrocardiograph 1 measures the cardiac potential waveform of a subject, and outputs the time-series signal string of the cardiac potential waveform (step S100 of FIG. 2). The storage unit 3 stores the time-series signal string of the cardiac potential waveform output from the electrocardiograph 1.

As is well known, the cardiac potential waveform is formed from continuous heartbeat waveforms, and one heartbeat waveform is formed from components such as P, Q, R, S, and T waves reflecting the activities of atriums and ventricles. The R-wave amplitude detection unit 5 detects the amplitude of the R wave from the signals of the cardiac potential waveform stored in the storage unit 3 (step S101 of FIG. 2). As a method of recognizing the R wave of the cardiac potential waveform, there is provided, for example, a technique disclosed in Japanese Patent Laid-Open No. 2003-561. This technique recognizes an R wave using a threshold based on an amplitude between the peak and valley of the cardiac potential waveform. The R-wave amplitude detection unit 5 detects an amplitude for each R wave of the cardiac potential waveform.

The R-R interval detection unit 6 detects an R-R interval from the signals of the cardiac potential waveform stored in the storage unit 3 (step S102 of FIG. 2). As a technique of detecting the R-R interval of the cardiac potential waveform, for example, there is provided a technique disclosed in "ECG Implementation on the TMS320C5515 DSP Medical Development Kit (MDK) with the ADS1298 ECG-FE", Texas Instruments Incorporated, <http://www.ti.com/lit/an/sprabj1/sprabj1.pdf>, 2011. This technique obtains an R-R interval based on a change in value of the time difference of the cardiac potential waveform. The R-R interval detection unit 6 detects an R-R interval for each R wave of the cardiac potential waveform.

On the other hand, the triaxial accelerometer 2 is mounted on the chest of the subject, and detects a triaxial acceleration by the respiratory motion of the subject and outputs the time-series signal string of the triaxial acceleration (step S103 of FIG. 2). The storage unit 4 stores the time-series signal string of the triaxial acceleration output from the triaxial accelerometer 2.

The acceleration displacement detection unit 7 detects the angular displacement of an acceleration vector from the signals of the triaxial acceleration stored in the storage unit 4 (step S104 of FIG. 2). To detect the angular displacement, after defining an acceleration variation surface from the average of the acceleration displacements in three axial directions, that is, the X, Y, and Z directions, the angle of a projection vector obtained when an acceleration vector formed from a combination of the acceleration data of the three axes in the X, Y, and Z directions is projected on the variation surface is calculated as the angular displacement. This method is disclosed in, for example, A. Bates, M. J. Ling, J. Mann and D. K. Arvind, "Respiratory rate and flow waveform estimation from tri-axial accelerometer data", International Conference on Body Sensor Network, pp. 144-150, June 2010. The acceleration displacement detection unit 7 detects an angular displacement for each sampling period of the acceleration.

Subsequently, the sampling unit 8 samples each of the time-series signal of the R-wave amplitude output from the R-wave amplitude detection unit 5, the time-series signal of the R-R interval output from the R-R interval detection unit 6, and the time-series signal of the angular displacement output from the acceleration displacement detection unit 7 at a sampling frequency (for example, a 1-Hz interval) lower than the sampling frequency of the electrocardiograph 1 and that of the triaxial accelerometer 2 (step S105 of FIG. 2).

The bandpass filter 9 limits the band of each of the time-series signal of the R-wave amplitude, that of the R-R interval, and that of the angular displacement, all of which have been acquired by the sampling unit 8 (step S106 of FIG. 2). The reason why the bandpass filter 9 is used is that the respiration frequency of a person is limited to only a low frequency. The pass band of the bandpass filter 9 is, for example, 0.15 to 0.4 Hz.

After multiplying, by a Hamming window function, each of the time-series signal of the R-wave amplitude, that of the R-R interval, and that of the angular displacement, whose band has been limited by the bandpass filter 9, the Fourier transform unit 10 performs fast Fourier transform for each of the time-series signal of the R-wave amplitude, that of the R-R interval, and that of the angular displacement, thereby obtaining the frequency spectrum of each of the signals of the R-wave amplitude, the R-R interval, and the angular displacement (step S107 of FIG. 2). As is well known, the Hamming window function is used to cut desired input data. The Fourier transform unit 10 performs such Fourier transform for each sampling period of the sampling unit 8. The number of data used for Fourier transform is, for example, 128 points (128 sec).

The signal selection unit 11 extracts a frequency as a candidate of the respiration frequency of the subject from each of the frequency spectrum of the R-wave amplitude, that of the R-R interval, and that of the angular displacement, all of which have been obtained by the Fourier transform unit 10, and selects the best data from the frequencies as the respiration frequency of the subject, thereby outputting a respiration frequency signal (step S108 of FIG. 2).

Figure 3:
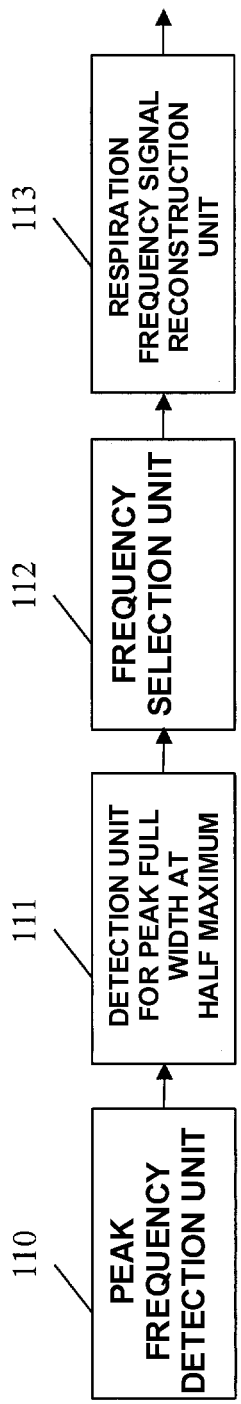
FIG. 3 is a block diagram showing the arrangement of a signal selection unit of the respiration estimation apparatus according to the embodiment of the present invention.

FIG. 3 is a block diagram showing the arrangement of the signal selection unit 11. FIG. 4 is a flowchart for explaining the operation of the signal selection unit 11. The signal selection unit 11 includes a peak frequency detection unit 110, a detection unit 111 for a peak full width at half maximum, a frequency selection unit 112, and a respiration frequency signal reconstruction unit 113.

The peak frequency detection unit 110 detects a peak frequency of each of the frequency spectrum of the R-wave amplitude, that of the R-R interval, and that of the angular displacement, all of which have been obtained by the Fourier transform unit 10 (step S200 of FIG. 4). When a plurality of peaks are detected for one frequency spectrum, the peak frequency detection unit 110 selects the frequency of the peak whose intensity is the maximum.

Subsequently, the detection unit 111 detects the full width at half maximum of the peak detected by the peak frequency detection unit 110 for each of the frequency spectrum of the R-wave amplitude, that of the R-R interval, and that of the angular displacement (step S201 of FIG. 4). The full width at half maximum indicates the width of the frequency at which the intensity is 50% of the peak intensity in the waveform of the peak detected by the peak frequency detection unit 110.

FIG. 5A shows an example of the frequency spectrum when the SN ratio is high, and FIG. 5B shows an example of the frequency spectrum when the SN ratio is low. Note that FIGS. 5A and 5B are graphs obtained by normalizing the intensity on the ordinate. In this example, normalization is performed by obtaining an area by integrating the power of each frequency (accumulating discrete values) so that the area of the power spectrum is 1. The power spectrum is obtained by cutting, for example, a section of 30 sec from the measured time-series data, and performing Fourier transform. In general, the breathing rate fluctuates but stays constant while it is stable, and has a peak P at a given frequency. The peak P of the respiration frequency is normally considered to fall within the range of about 0.2 to 0.4 Hz. However, a full width W at half maximum of the peak tends to extend due to the influence of the body motion and autonomic nervous system of the subject. It is considered that as the full width W at half maximum is narrower, the respiration detection accuracy is higher.

The frequency selection unit 112 selects, as the respiration frequency of the subject, the peak frequency at which the full width at half maximum detected by the detection unit 111 is equal to or smaller than a predetermined threshold (for example, 0.0625 Hz) among the three peak frequencies (the peak frequency of the R-wave amplitude, that of the R-R interval, and that of the angular displacement) detected by the peak frequency detection unit 110 (step S202 of FIG. 4), and discards the unselected peak frequencies (step S203 of FIG. 4).

When there are a plurality of peak frequencies at which the full width at half maximum is equal to or smaller than the predetermined threshold (for example, the full width at half maximum of the R-wave amplitude and that of the angular displacement are equal to or smaller than the threshold), the frequency selection unit 112 selects, as the respiration frequency, the peak frequency at which the full width at half maximum is narrower. Note that if all the three full widths at half maximum (the full width at half maximum of the R-wave amplitude, that of the R-R interval, and that of the angular displacement) exceed the predetermined threshold, the frequency selection unit 112 performs processing based on an assumption that data of the current data point at which the respiration frequency is to be confirmed is defective.

The respiration frequency signal reconstruction unit 113 generates a respiration frequency signal string by arranging, in time-series, the data of the respiration frequencies selected by the frequency selection unit 112 (step S204 of FIG. 4), and outputs it. Note that when the data of the respiration frequency at given time is defective, the respiration frequency signal reconstruction unit 113 complements the data by using the data of the respiration frequency at immediately preceding time (one sampling period before).

The signal selection unit 11 performs the above processing for each sampling period of the sampling unit 8 (every second in the example of this embodiment).

Figure 6:
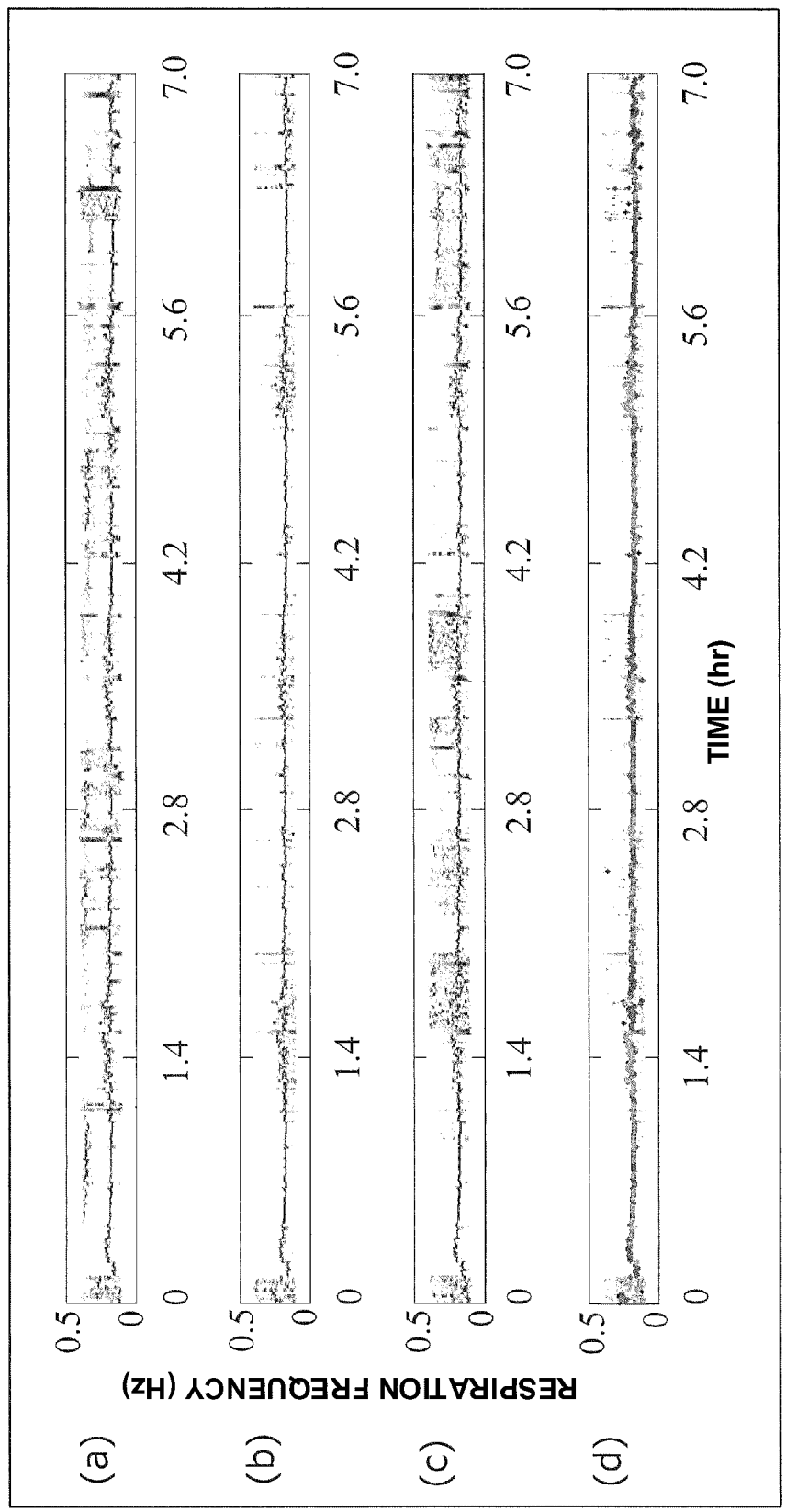
FIG. 6 shows timing charts of respiration frequency signal strings each obtained when each of the peak frequencies of an angular displacement, an R-R interval, and an R-wave amplitude is selected as a respiration frequency, and a respiration frequency signal string obtained by the respiration estimation apparatus according to the embodiment of the present invention.
Figure 7:
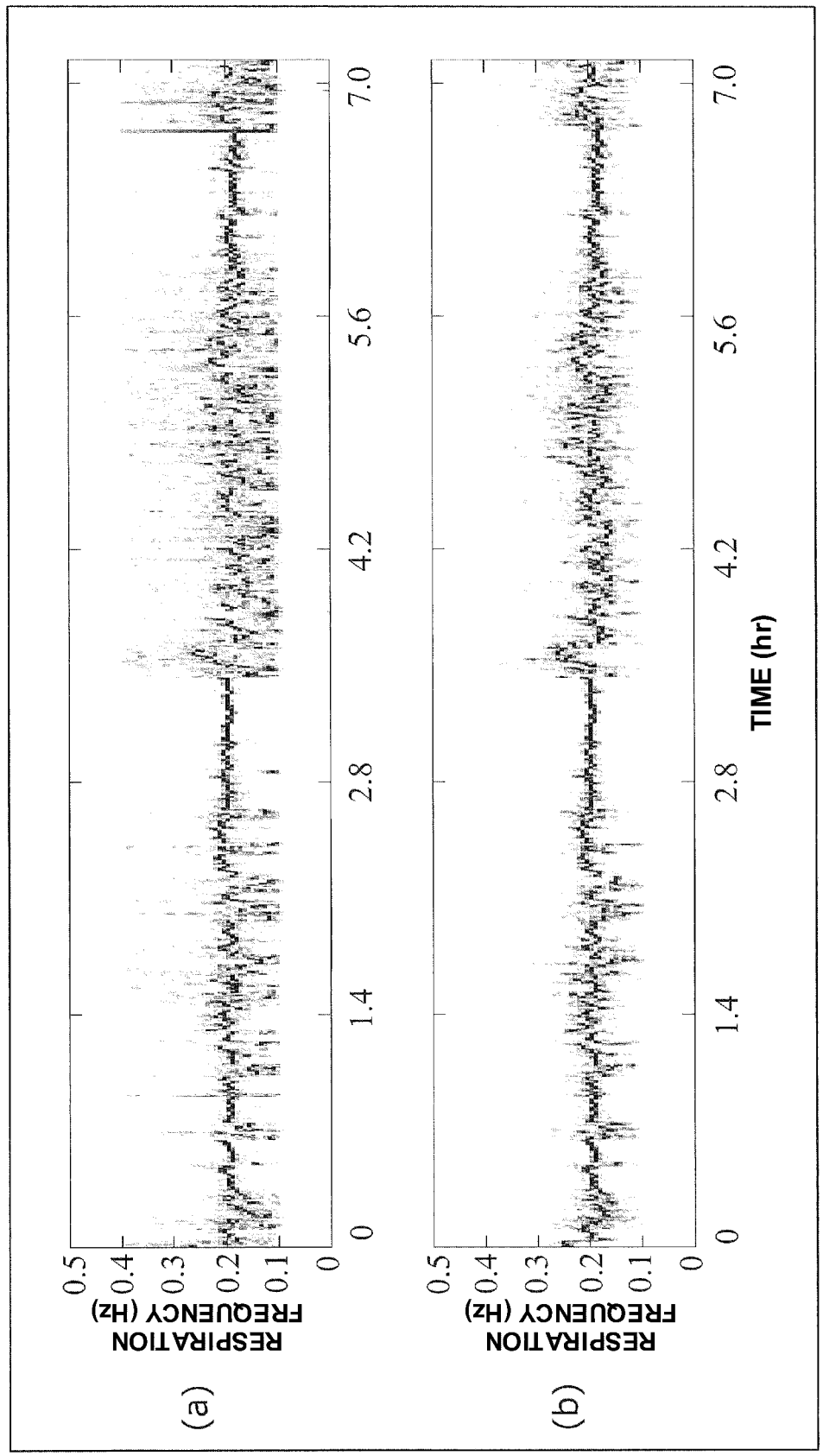
FIG. 7 shows timing charts of a respiration frequency signal string obtained by the respiration estimation apparatus according to the embodiment of the present invention and a respiration frequency signal string obtained by a related respiration sensor.
Figure 8:
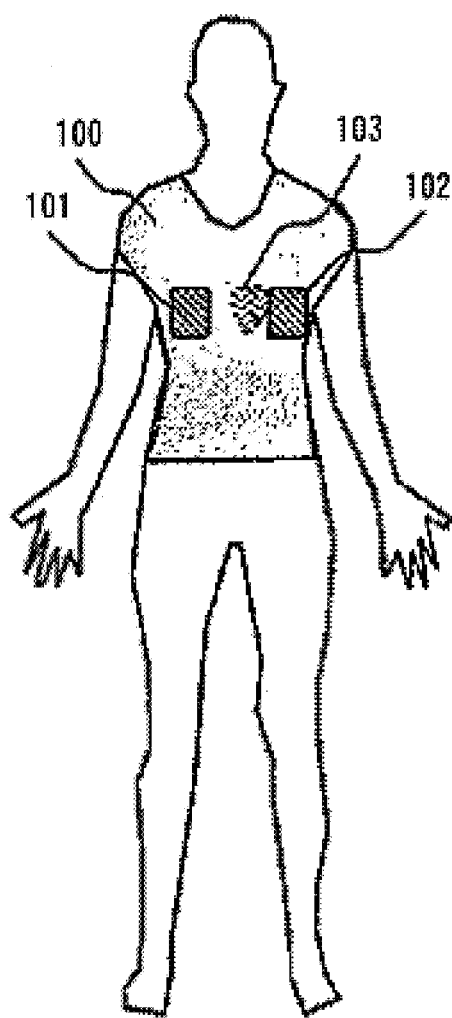
FIG. 8 is a schematic view showing a state in which a wearable sensor is mounted on a human body.

In FIG. 6, (a) is timing chart showing a respiration frequency signal string obtained when the peak frequency of the angular displacement is selected as a respiration frequency, (b) is a timing chart showing a respiration frequency signal string obtained when the peak frequency of the R-R interval is selected as a respiration frequency, (c) is a timing chart showing a respiration frequency signal string obtained when the peak frequency of the R-wave amplitude is selected as a respiration frequency, and (d) is a timing chart showing a respiration frequency signal string obtained by the respiration estimation apparatus according to this embodiment. In FIG. 7, (a) is a timing chart showing a respiration frequency signal string obtained by the respiration estimation apparatus according to this embodiment, and (b) is a timing chart showing a respiration frequency signal string obtained by a related respiration sensor.

The actual measured value of the respiration frequency measured by the respiration sensor is at about 0.2 Hz. As is apparent from (a) of FIG. 7, according to this embodiment, it is understood that the transition of the respiration frequency which matches the result obtained by the respiration sensor is obtained.

According to this embodiment, the respiration frequency of the subject is estimated by integrating the plurality of sensor data and extracting the best data in order to cope with the individual difference of the age, autonomic nervous system, skin condition, and body structure of the subject.

In a case in which data of the triaxial acceleration is used to estimate the respiration frequency, it is difficult to exclude a measurement error caused by the individual difference of a body motion or body structure. When data of the R-R interval is used to estimate the respiration frequency, there is restriction on calculation of a respiration cycle by the cardiac cycle, and it is thus difficult to exclude a measurement error caused by the influence of the autonomic nervous system that changes depending on the mental condition and age. When data of the R-wave amplitude is used to estimate the respiration frequency, it is difficult to exclude a measurement error caused by the individual difference of the skin condition, a change in contact impedance in accordance with the body motion or skin condition, or the like. To the contrary, in this embodiment, even if the S/N ratio degrades, it is possible to estimate the respiration frequency by selecting the best data from the plurality of sensor data.

The storage units 3 and 4, R-wave amplitude detection unit 5, R-R interval detection unit 6, acceleration displacement detection unit 7, sampling unit 8, bandpass filter 9, Fourier transform unit 10, and signal selection unit 11, all of which have been described in this embodiment, can be implemented by a computer including a CPU (Central Processing Unit), a storage device, and an interface, and a program for controlling these hardware resources. The CPU executes the processing described in this embodiment in accordance with programs stored in the storage device.

Note that the electrocardiograph 1 includes an electrode attached to clothing such as a shirt, and a cardiac potential waveform signal processing unit in a monitoring apparatus attached to the clothing, and the electrode and the cardiac potential waveform signal processing unit are connected by a wiring line. Similarly, the triaxial accelerometer 2 includes a sensor unit attached to the clothing and an acceleration signal processing unit provided in the monitoring apparatus, and the sensor unit and the acceleration signal processing unit are connected by a wiring line.

In this embodiment, the electrocardiograph 1 and the triaxial accelerometer 2 may be provided together with or separately from the wearable device attached to the clothing. That is, the storage units 3 and 4, R-wave amplitude detection unit 5, R-R interval detection unit 6, acceleration displacement detection unit 7, sampling unit 8, bandpass filter 9, Fourier transform unit 10, and signal selection unit 11 may be provided in the monitoring apparatus or provided in another apparatus. When the storage units 3 and 4, R-wave amplitude detection unit 5, R-R interval detection unit 6, acceleration displacement detection unit 7, sampling unit 8, bandpass filter 9, Fourier transform unit 10, and signal selection unit 11 are provided in another apparatus, a cardiac potential waveform signal obtained by the electrocardiograph 1 and a triaxial acceleration signal obtained by the triaxial accelerometer 2 are wirelessly transmitted to the apparatus.

INDUSTRIAL APPLICABILITY

The present invention is applicable to continuous respiratory monitoring of continuously observing breathing of a person.

EXPLANATION OF THE REFERENCE NUMERALS AND SIGNS

1 . . . electrocardiograph, 2 . . . triaxial accelerometer, 3, 4 . . . storage unit, 5 . . . R-wave amplitude detection unit, 6 . . . R-R interval detection unit, 7 . . . acceleration displacement detection unit, 8 . . . sampling unit, 9 . . . bandpass filter, 10 . . . Fourier transform unit, 11 . . . signal selection unit, 110 . . . peak frequency detection unit, 111 . . . detection unit for peak full width at half maximum, 112 . . . frequency selection unit, 113 . . . respiration frequency signal reconstruction unit.

The invention claimed is:

1. A respiration estimation apparatus comprising:
an R-wave amplitude detection circuit which detects an amplitude of an R wave from a cardiac potential waveform of a subject;
an R-R interval detection circuit which detects an R-R interval as an interval between an R wave and an immediately preceding R wave from the cardiac potential waveform of the subject;
an acceleration displacement detection circuit which detects an angular displacement of an acceleration vector at a chest of the subject from a triaxial acceleration signal caused by a respiratory motion of the subject;
a processor which Fourier-transforms each of a time-series signal of the R-wave amplitude over time, a time-series signal of the R-R interval over time, and a time-series signal of the angular displacement over time to obtain a frequency spectrum of each of the signals of the R-wave amplitude, the R-R interval, and the angular displacement; and a signal selection circuit, wherein the signal selection circuit includes:

a first detection circuit which extracts a peak frequency from each of the frequency spectrum of the R-wave amplitude, the frequency spectrum of the R-R interval, and the frequency spectrum of the angular displacement, as candidates of the respiration frequency of the subject, a second detection circuit which detects a full width at half maximum of the peak frequency detected by the first detection circuit, for each of the frequency spectrum of the R-wave amplitude, the frequency spectrum of the R-R interval, and the frequency spectrum of the angular displacement, and a frequency selection circuit which selects, as the respiration frequency of the subject, a peak frequency at which the full width at half maximum extracted by the second detection circuit is not larger than a predetermined threshold taken from a memory among the three peak frequencies detected by the first detection circuit, wherein when there are a plurality of peak frequencies at which the full width at half maximum is not larger than the predetermined threshold, the frequency selection circuit selects, as the respiration frequency, the peak frequency at which the full width at half maximum is the narrowest of all the peak frequencies, the signal selection circuit further being configured to display a respiration frequency signal representing the respiration frequency of the subject over time; and when all the three full widths at half maximum exceed the predetermined threshold, the frequency selection circuit determines that data including the cardiac potential waveform and the triaxial acceleration signal is defective.

2. The respiration estimation apparatus according to claim 1, further comprising:

a sampling circuit which samples each of the time-series signal of the R-wave amplitude obtained by the R-wave amplitude detection circuit, the time-series signal of the R-R interval obtained by the R-R interval detection circuit, and the time-series signal of the angular displacement obtained by the acceleration displacement detection circuit at a sampling frequency lower than a sampling frequency of the cardiac potential waveform and a sampling frequency of the triaxial acceleration signal; and a bandpass filter configured to limit a band of each of the sampled time-series signal of the R-wave amplitude, the sampled time-series signal of the R-R interval, and the sampled time-series signal of the angular displacement, wherein the processor Fourier-transforms each of the bandpass filtered time-series signal of the R-wave amplitude, the bandpass filtered time-series signal of the R-R interval, and the bandpass filtered time-series signal of the angular displacement.

* * * * *